United States Patent [19]

Eryman et al.

[11] Patent Number: 5,177,277
[45] Date of Patent: Jan. 5, 1993

[54] HYDROGENATED DEODORIZED POLYBUTENE POLYMERS

[75] Inventors: William S. Eryman, Naperville, Ill.; James B. Lents, Benton, Ky.; Yin-Chou Lin, Naperville, Ill.; Thomas E. Rehm, Aurora, Ill.; Egils Vitands, Lisle, Ill.

[73] Assignee: Amoco Corporation, Chicago, Ill.

[21] Appl. No.: 805,841

[22] Filed: Dec. 4, 1991

[51] Int. Cl.⁵ .................. C07C 7/04; C07C 7/163
[52] U.S. Cl. .................. 585/255; 585/264; 585/802; 585/823; 585/841
[58] Field of Search ........... 585/250, 255, 259, 823, 585/264, 802, 841

[56] References Cited

U.S. PATENT DOCUMENTS

| | | | |
|---|---|---|---|
| 3,100,808 | 8/1963 | Dyer | 260/683.9 |
| 4,061,780 | 12/1977 | Yoshida et al | 424/358 |
| 4,423,264 | 12/1983 | Juguin et al. | 585/255 |
| 4,795,482 | 1/1989 | Gioffre et al. | 55/75 |
| 4,923,961 | 5/1990 | Vitands et al. | 585/824 |
| 5,043,420 | 8/1991 | Vitands et al. | 585/255 |

FOREIGN PATENT DOCUMENTS 124602  7/1985  Japan .................... 585/250

Primary Examiner—Anthony McFarlane
Attorney, Agent, or Firm—Rae K. Stuhlmacher; Wallace L. Oliver; Frank J. Sroka

[57] ABSTRACT

A process for the preparation of hydrogenated deodorized polybutene polymers, wherein the polybutene polymer is hydrogenated, distilled to substantially remove low boiling odorous compounds, and treated with silica gel to substantially remove the remaining odorous compounds thereby providing an improved hydrogenated, distilled, silica gel-treated polybutene polymer substantially free of odorous compounds.

11 Claims, No Drawings

HYDROGENATED DEODORIZED POLYBUTENE POLYMERS

FIELD OF THE INVENTION

This invention relates to a process for the preparation of hydrogenated deodorized $C_4$ olefin polymers. More specifically, the present invention relates to the preparation of deodorized polybutene polymers wherein the polybutene polymer is hydrogenated, distilled to substantially remove low boiling odorous compounds, and treated with silica gel to substantially remove the remaining odorous compounds thereby providing an improved hydrogenated, distilled, silica gel-treated polybutene polymer substantially free of odorous compounds.

BACKGROUND OF THE INVENTION

Squalane, obtained from natural sources, is one of the more common moisturizer agents used in dermatological preparations and is useful as a base oil for cosmetics. However, the production is low, the price is high, and the quality is not uniform. These problems make it desirable to find a squalane substitute.

$C_4$ olefin polymers of a number average molecular weight range of from about 100 to about 4,000 g/mol are desirable for use in cosmetics and antiperspirants. The molecular weight range assures compatibility with many of the components found in these preparations. However, these $C_4$ olefin polymers are normally light colored and carry an oily to pungent odor, both of which are undesirable in cosmetics and antiperspirants. While these characteristics may not be significant in industrial applications, such characteristics render the $C_4$ olefin polymers unfit for more sensitive uses, such as cosmetics and antiperspirants, which require an essentially colorless and odorless product. As a topical application, a cosmetics and antiperspirants cannot have, or develop, offensive odors even though the preparation may contain perfume to add a pleasing fragrance.

Hydrogenation to produce a saturated compound of $C_4$ olefin polymers, such as polybutene polymer, is taught in U.S Pat. No. 3,100,808 (fully incorporated herein by reference), to improve the color and odor of the resulting saturated polymer. However, although the hydrogenation process may reduce the odor and color in the $C_4$ olefin polymers, the hydrogenated polymer can still contain odor-causing compounds, such as aldehydes, ketones, esters and peroxides.

U.S. Pat. No. 4,061,780 (Yoshida, et al.) teaches purification of $C_4$ olefin polymers for use in cosmetic applications wherein a liquid $C_4$ olefin fraction is polymerized in the presence of a catalyst. The polymerized reaction product is fractionally distilled to obtain a fraction having a boiling point range of from 120° C. (248° F.) to 200° C. (392° F.) at 1-2 mmHg to remove compounds having a molecular weight of less than about 250 g/mol and compounds having a molecular weight of more than 600 g/mol. The resulting fraction is hydrogenated and deodorized by steam distillation under reduced pressure, treatment with activated carbon, solvent extraction, or by a combination of steam distillation, treatment with activated carbon and solvent extraction. The initial distillation of the $C_4$ polymer fraction is taught as removing compounds which can easily oxidize to form odorous compounds. This procedure is an economically costly commercial process.

Japanese Kokai Patent No. Sho 60[1985]-124602 discloses a manufacturing method for butylene polymer in the molecular weight range of 100-300 g/mol. The polybutene polymer is not hydrogenated. The polybutene is treated with a silicon-alumina adsorbent to decrease odor in the polymer for applications such as insecticide solvent or copier solvent.

U.S. Pat. No. 4,923,961, fully incorporated herein by reference, discloses deodorized polymers of $C_4$ olefins that demonstrate an improved storage and color stability at temperatures of up to 200° F. for extended periods. The $C_4$ olefin polymer is hydrogenated and deodorized by nitrogen stripping to remove a portion of the hydrogenated product and by contacting the stripped product with attapulgite clay in a ratio of product to clay of 1:1 to 10:1. However, there is a large product loss, up to 24 percent, when the hydrogenated, nitrogen stripped polybutene polymer is deodorized with attapulgite clay. Further, regeneration and reuse of the attapulgite clay is not a viable alternative. Therefore, it would be advantageous to provide a method of manufacturing a deodorized polybutene polymer that reduces product loss and that includes the ability to regenerate and reuse the material used in the deodorizing step.

Accordingly, it is an object of the present invention to provide an improved process for production of hydrogenated deodorized polybutene polymer.

It is another object of the present invention to provide a process for the preparation of deodorized substantially saturated polybutene polymers of a number average molecular weight of from about 100 to about 4,000 g/mol wherein the polybutene polymers are substantially free of odor-causing compounds such as aldehydes, ketones, esters and peroxides, and are suitable for replacement of squalane, fatty esters, and other moisturizing agents used in cosmetics and antiperspirants.

It is still a further object of the present invention to provide a process that can be in batch or continuous mode, that is not complex in operation, that uses readily available process equipment, and that includes an adsorption medium that is easily regenerated such that the adsorption medium can be reused in future deodorizing processes.

SUMMARY OF THE INVENTION

The present invention is a process for the production of hydrogenated deodorized polybutene polymer. Polybutene polymer is hydrogenated and the hydrogenated polybutene polymer is distilled at a temperature of from about 290° F. to about 370° F. and at a pressure of no more than 10 mmHg (absolute), preferably from about 3 mmHg to about 5 mmHg (absolute), to remove the lower boiling odorous compounds. The amount of low boiling odorous compounds that are removed will vary according to the molecular weight distribution of the hydrogenated polybutene. Typically, from about 0.5 wt.% to about 5 wt.% of the material that is charged into the distillation system is removed (as overhead). When less than about 0.5 wt.% of the charge is removed from the distillation system, not enough of the odor-causing compounds are removed and the hydrogenated polybutene polymer can still have an unpleasant odor. When more than about 5 wt.% of the charge is removed from the distillation system, the process begins to become economically unattractive. Typically, the best results are obtained when between about 2 wt.% and about 4 wt.% of the material that is charged into the distillation system is removed.

The main distillate fraction is treated with silica gel at a temperature of less than about 150° F. wherein the ratio of hydrogenated distilled polybutene polymer to silica gel is from about 25:1 to about 200:1, preferably from about 50:1 to about 100:1, depending on the size and type of silica gel that is used in the process. For example, where a 28-200 mesh (0.0232-0.0029 inch) silica gel is used, it was found that the preferred hydrogenated distilled polybutene polymer to silica gel ratio was from about 50:1 to about 100:1. It has been found that as the ratio was decreased to below a ratio of hydrogenated distilled polybutene polymer to silica gel of about 50:1 there was not a significant improvement in the deodorization of the hydrogenated distilled polybutene polymer.

The process of the present invention can be in batch or continuous mode, is not complex in operation, uses readily available process equipment, and includes an adsorption medium that is easily regenerated such that the adsorption medium can be reused in future deodorizing processes.

The process of the present invention provides deodorized substantially saturated polybutene polymers of a number average molecular weight of from about 100 to about 4,000 g/mol, haze —5 APHA max, haze-free color —10 APHA max, and bromine index —1,000 max, wherein the polybutene polymers are substantially free of odor-causing aldehydes, ketones, esters and peroxides, and are suitable for replacement of squalane, fatty esters, and other moisturizing agents used in cosmetics and antiperspirants.

DESCRIPTION OF THE INVENTION

Briefly, the $C_4$ olefin polymers of the present invention are prepared by polymerizing a mixture of $C_4$ olefins by methods that are well known in the art to obtain a $C_4$ olefin polymer with a number average molecular weight range of from about 100 to about 4,000 g/mol. Generally speaking, the polymerization reaction is a Friedel-Crafts reaction using a catalyst such as aluminum chloride or boron trifluoride and is disclosed extensively in the patent and technical literature. The hydrocarbon feedstock may be a refinery fraction, a pure monoolefin, or a mixture of monoolefins. Monoolefin feedstock where the olefin contains 3 to 16 carbon atoms is preferred. If a pure olefin is used which is gaseous under ambient conditions it is necessary either to control the reaction pressure or to dissolve the olefin in a solvent medium, inert under the reaction conditions, in order to maintain the olefin in the liquid phase. In the case of isobutylene, which is typical of monoolefins, the feedstock used in the polymerization process may be pure isobutylene or a mixed $C_4$ hydrocarbon feedstock such as that resulting from the thermal or catalytic cracking operation. This is a liquid when under pressure and hence no diluent is needed. The feedstock used may contain between 5 and 100% by weight of isobutylene. It is preferred to use a feedstock containing at least about 10% by weight of isobutylene. The hydrocarbon feedstock used may contain, in addition to isobutylene, butanes, butenes, and minor amounts of polymerization byproducts without adverse effect on the polybutene product.

The polymerization temperature is selected based on the molecular weight desired in the product. As is well known, lower temperatures are used for higher molecular weights while higher temperatures are used to obtain lighter products. The polymerization can be carried out in the full range of temperatures generally associated with conventional polybutene polymerization, i.e., about −100° C. to about 50° C.

The resulting $C_4$ olefin polymer typically includes various forms of butene, for example isobutene, 1-butene, trans-2-butene, cis-2-butene, and can contain a small amount of propene and minor amounts of polymerization byproducts. For simplicity, the typical polymer is referred to herein as polybutene polymer. Typically, isobutene constitutes from about 80% to about 95% of the total polybutene polymer. The polybutene polymer has at least one double bond per molecule.

Hydrogenation is understood to mean that the double bonds of the polybutene polymer are substantially saturated with hydrogen. The hydrogenation step typically provides a product that contains odorous compounds. The hydrogenated polybutene polymer is distilled under a vacuum of from about 3 mmHg (absolute) to about 5 mmHg (absolute) at a temperature of at least about 290° F. to remove a portion of the odorous compounds. Then, the hydrogenated distilled polybutene polymer is contacted with silica gel in a hydrogenated distilled polybutene polymer to silica gel ratio of from about 25:1 to about 200:1, preferably from about 50:1 to about 100:1, at a temperature of less than about 150° F. to substantially remove the remaining odorous compounds.

The product is a hydrogenated, substantially deodorized polybutene polymer having a number average molecular weight range of from about 100 to about 4,000 g/mol, haze —5 APHA max, haze-free color —10 APHA max, bromine index —1,000 max, is substantially free of odor-causing aldehydes, ketones, esters and peroxides, and is suitable for use in cosmetics and antiperspirants.

The number average molecular weight range of from about 100 to about 4,000 g/mol advantageously provides lighter molecular weight ends to readily solubilize other compounds in cosmetic and antiperspirant formulations. The heavier molecular weight range lends body to the final preparation when the product is used as a base oil in place of, for example, squalane, in conventional oil-based cosmetic compositions such as creams, lotions, hair oils, suntan products, baby oil, lip glosses, and the like.

In greater detail, hydrogenation of polybutene polymer is described in U.S. Pat. No. 3,100,808, fully incorporated herein by reference. Hydrogenation of the polybutene polymers can be at a temperature within the range of from about 150° F. to 525° F. with hydrogen gas at a pressure ranging from about atmospheric to about 3,000 psi for a period ranging from about one minute, under strong hydrogenating conditions, up to many hours, preferably in the presence of a catalyst. Preferred hydrogenation catalysts include nickel, platinum, palladium, and the like. The hydrogenation step produces a substantially saturated polybutene polymer.

The original feedstock may contain odorous compounds as well as other compounds which under hydrogenation can further form odor and color-forming compounds. These compounds are generally considered to be aldehydes, ketones, esters, and peroxides. It has been found that removal of the odor-causing compounds from a hydrogenated polybutene polymer of from about 100 to about 4,000 g/mol number average molecular weight can be accomplished by distilling the hydrogenated polybutene polymer, and further treating the hydrogenated, distilled polybutene polymer with silica gel to provide a hydrogenated deodorized polybutene polymer.

Hydrogenation of the polybutene polymers of a number average molecular weight of from about 100 to about 4,000 g/mol, followed by distillation to substantially remove the lighter boiling odorous compounds, typically from about 0.5 wt.% to about 5 wt.% of the material that is charged into the distillation system (preferably from about 2 wt.% to about 4 wt.%), and then treatment with silica gel to substantially remove the remaining odorous compounds produces a deodorized hydrogenated polybutene polymer having haze —5 APHA maximum, haze-free color —10 APHA maximum and bromine index —1,000 maximum.

The odorous compounds contained in the polybutene polymer could not be isolated, identified, and accurately measured by chromatography techniques, nor any other instrumental techniques. However, when the head space was analyzed by gas chromatography analysis it was found that several peaks were present before the polybutene polymer was processed according to the present invention and were reduced, or disappeared, after processing (see Example 5 and Table I). Since this analysis was not able to accurately detect and measure the odorous compounds, an odor panel was used to detect the presence or absence of odor in the finished product.

Distillation as used herein refers to the typical distillation set-up as is well known in the art. Typically, a still pot is charged with a material (charge material) to be distilled. Heat is applied to the material in the still pot to effect the removal of the lower boiling compounds in the charge material (overhead fraction). In the present case, the distillation can take place under a vacuum of from about 3 mmHg (absolute) to about 5 mmHg (absolute) and a temperature of from about 290° F. to about 370° F. An inert gas, such as nitrogen can be supplied. The portion of the total charge material that is removed is referred to as the distillate, or overhead fraction, and the portion of the total charge material that remains is referred to as the main fraction or main distillate fraction (bottom fraction).

In the present invention, the total overhead fraction removed is typically from about 0.5 wt.% to about 5 wt.% of the total charge material. Distilling off less than about 0.5 wt.% has been found to be ineffective in significantly reducing the level of odorous compounds present in the hydrogenated polybutene polymer. Distilling off more than about 5 wt.% has been found to be uneconomical.

Steam distillation would not be a viable alternative in the process of the present invention due to the probability of water remaining in the hydrogenated steam distilled polybutene polymer. The addition of water to the process would inactivate the silica gel thereby decreasing the deodorization capacity of the silica gel.

In the present invention, the main distillate fraction is treated with silica gel to essentially adsorb residual odor components remaining after the distillation step. Silica gel treatment processing can be accomplished either by slurrying the silica gel with the main distillate fraction or by passing the main distillate fraction through a fixed bed of silica gel.

Silica gel particle size is commonly identified in the silica gel industry as a "mesh" size. This method of particle size measurement is based on the "Tyler" standard screen scale. Mesh size is typically stated as less than, or greater than, a particular mesh size. For convenience, the corresponding measurement in inches is provided herein parenthetically.

Silica gel that is used in slurry processing can be of a small particle size, since removal (isolation) of the silica gel is typically accomplished by filtration or centrifugation following the slurry adsorption processing. Silica gel used in fixed bed processing must be of somewhat larger particle size to allow for an economical adsorption processing rate. For example, silica gel used in fixed bed processing can be of a particle size greater than 140 mesh (0.0043 inch) and less than about 5 mesh (0.156 inch). The same silica gel used in fixed bed processing can be used in slurry processing. In addition, silica gel smaller than 140 mesh (0.0043 inch) can be used in slurry processing.

The silica gel can be regenerated by any of the numerous techniques which are well known in the art. Further description of the various regeneration methods can be found in Schweitzer, Editor, "Handbook Separation Techniques for Chemical Engineers", McGraw-Hill (1979); and Green, Editor, "Perry's Chemical Engineers' Handbook", 6th Edition, McGraw-Hill (1984), both of which are fully incorporated herein by reference. Some examples of regeneration techniques are:

A) Thermal swing — heating the spent adsorbent to an elevated temperature so that the silica gel's capacity for the adsorbates is significantly reduced, while at the same time purging the silica gel with a gas;

B) Pressure swing — lowering the pressure at essentially constant temperature to reduce the silica gel's capacity for the adsorbates;

C) Solvent wash — passing a liquid or gas, (for example, methylene chloride or methanol) for which the adsorbates are highly soluble or miscible, through the silica gel;

D) Displacement adsorption — passing a liquid through the silica gel which has a higher affinity for the silica gel than the adsorbates wherein the liquid is subsequently removed by a different regeneration method;

E) Controlled burnoff — this method is essentially a controlled oxidation of the adsorbates using a gas stream with low-oxygen concentration.

The final product is a hydrogenated, deodorized polybutene polymer cosmetic base oil which is a bright, clear, odorless viscous liquid which is stable for long periods of time, not demonstrating any degradation due to oxidation over storage periods of up to one year under ambient temperature conditions, contains no cyclic compounds, is miscible with mineral oils and organic solvents, matches the feel and moisturizing ability of squalane, and is hydrophobic but is easily emulsified.

This cosmetic base oil is typically used in amounts of up to about 25-40 wt.% or higher in cosmetic formulations requiring an oil-base composition in accordance with conventional practice. For example, baby oil can contain almost 100 wt.% of the cosmetic base oil.

In summary, a hydrogenated polybutene polymer having a number average molecular weight of from about 100 to 4,000 g/mol is distilled at a temperature of from about 290° F. to about 370° F. and at a pressure of no more than 10 mmHg (absolute). Thereafter, the higher boiling portion of the hydrogenated polybutene polymer distillation product is treated with a silica gel at a temperature of less than about 150° F. to produce a hydrogenated distilled polybutene polymer substantially free of odorous compounds.

In greater detail, the process of the present invention comprises a method for deodorizing an odorous polybutene polymer, of molecular weight of from about 100 to about 4,000 g/mol which comprises:

A) hydrogenating polybutene polymer at a temperature of from about 150° F. to about 525° F. in the presence of a catalyst, to form a substantially hydrogenated polybutene polymer containing odorous compounds;

B) distilling a hydrogenated polybutene polymer having a number average molecular weight of from about 100 to 4,000 g/mol at a temperature of from about 290° F. to about 370° F. and at a pressure of no more than 10 mmHg (absolute) to remove a portion of the odorous compounds, and to prepare a hydrogenated, distilled polybutene polymer;

C) treating the hydrogenated, distilled polybutene polymer with a silica gel wherein the ratio of the hydrogenated distilled polybutene polymer to the silica gel is from about 25:1 to about 200:1, preferably from about 50:1 to about 100:1, at a temperature of less than about 150° F. to remove additional odorous compounds and provide a hydrogenated, distilled, silica gel-treated polybutene polymer; and D) recovering the hydrogenated, distilled, silica gel-treated polybutene polymer substantially free of compounds and odorous compounds, having haze —5 APHA maximum, haze-free color —10 APHA maximum and of a molecular weight range of from about 100 to about 4,000 g/mol.

In still greater detail, the distillation will preferably remove from about 0.5 wt.% to about 5 wt.% of the material that is charged into the distillation system, more preferably from about 2 wt.% to about 4 wt.%. The silica gel preferably has a particle size of less than about 5 mesh (0.156 inch) and greater than about 140 mesh (0.0043 inch). The ratio of hydrogenated distilled polybutene polymer to silica gel preferably is from about 50:1 to about 100:1.

The following examples will serve to illustrate certain embodiments of the herein disclosed invention. These examples should not, however, be construed as limiting the scope of the invention as there are many variations which may be made thereon without departing from the spirit of the disclosed invention, as those of skill in the art will recognize.

EXAMPLES

Since the odorous compounds could not be isolated and accurately measured by chromatography techniques, an odor panel was used to assess odor.

EXAMPLE 1

The following illustrates the method of hydrogenating polybutene polymers of a number average molecular weight of from about 100 to about 4,000 g/mol.

The equipment used was a 1,000 gallon nickel reactor equipped with a radial turbine mixer, three anti-rotation baffles and a 4 foot square sparge ring. The reactor was thoroughly cleaned with water and dried with nitrogen and heat. About 5,000 pounds of polybutene polymers of molecular weight of from about 100 to about 4,000 g/mol and 25 pounds of 5% palladium on active carbon powder catalyst were placed in the reactor. The reactor, with stirring, was heated to about 340° F. with steam in the reactor jacket. The reactor was then pressurized with hydrogen to 350 psig. The temperature of the reactor contents continued to rise because of the heat generated by the hydrogenation reaction. Maximum temperature reached was about 470° F. The hydrogenation reaction was essentially complete after 6 hours. The reactor contents were then pumped through a filter precoated with celite. The final product had the following properties: viscosity —30.4 cSt (100° F.), flash point COC —280° F., color (APHA) —0.0, haze (APHA) 0.3, bromine index 387 (0.8% unsaturation). An odor panel found the odor to be unacceptable.

EXAMPLE 2

The following illustrates the distillation and silica gel treatment of a hydrogenated polybutene polymer of molecular weight of from about 100 to about 4,000 g/mol.

A 12-liter three-neck round-bottom flask equipped with electric heating mantle, thermowell, nitrogen sparge, 15-tray distillation column, distillate/reflux splitter, and condenser was charged with 7,525g of hydrogenated polybutene polymer (prepared in a manner described in Example 1), molecular weight of from about 100 to about 4,000 g/mol. The temperature was 370° F. Nitrogen gas at 0-1.1 standard cubic feet per hour (scfh) was bubbled through the polymer for a period of 8.5 hour. The overhead fraction was collected in a graduated cylinder. The distillation was conducted at 8 mmHg, absolute pressure.

An infrared analysis of the overhead fraction (2.5% was distilled off) indicated the presence of hydroxyl groups and carbonyl groups but the individual odorous compounds could not be accurately identified and measured by chromatography analysis.

After cooling, the main distillate fraction was submitted to an odor panel to detect any odor. A slight odor was detectable.

The main distillate fraction was cooled to a temperature of less than 100° F., percolated through a fixed bed of silica gel of 28-200 mesh (0.0232-0.0029 inch), and the hydrogenated distilled silica gel-treated polybutene polymer was isolated. The ratio of hydrogenated distilled polybutene polymer to silica gel was 50:1. The silica gel-treated material was clear and haze-free. No odor was detectable by an odor panel.

EXAMPLE 3

A hydrogenated polybutene polymer having a molecular weight range of from about 100 g/mol to about 4,000 g/mol was prepared in a manner similar to that described in Example 2. The hydrogenated polybutene polymer was distilled and then slurry treated with silica gel at a ratio of hydrogenated distilled polybutene polymer to silica gel of about 10:1 and the hydrogenated distilled silica gel-treated polybutene polymer was isolated. The hydrogenated distilled silica gel-treated polybutene polymer was clear and haze-free. The odor was minimal as determined by an odor panel.

COMPARATIVE EXAMPLE A

Hydrogenated polybutene polymer of molecular weight of about 100 to about 4,000 g/mol, was prepared in a manner described in Example 1. The hydrogenated polybutene polymer was treated with activated charcoal. Treatment with activated charcoal was ineffective in removing odor to an acceptable level. Details of the activated charcoal treatments are as follows:

A) Hydrogenated polybutene polymer of molecular weight of from about 100 to about 4,000 g/mol, 500 grams, was filtered in a single pass through 25 grams of Darco-60 activated charcoal in a 2 inch glass column maintained at room temperature. The odor panel determined that the filtered product had a persistent, unacceptable odor and had a dark color.

B) The procedure of charcoal treatment A) was repeated but the filtration was maintained at a temperature of 200° F. The odor panel determined that the filtered product had a persistent, unacceptable odor and had a dark color.

C) Hydrogenated polybutene polymer of molecular weight range of from about 100 to about 4,000 g/mol, 400 grams, and 25 grams of Darco C-60 activated charcoal were added to a suitable vessel equipped with stirring means to prepare a slurry. The mixture was slurred for one hour at room temperature with stirring and then the carbon was removed by filtration. The odor panel determined that the filtered product had a persistent, unacceptable odor.

D) The procedure of charcoal treatment C) was repeated at a temperature of 302-338° F. The carbon was removed by filtration. The odor panel determined that the filtered product had a persistent, unacceptable odor.

The above illustrates that use of activated charcoal alone is ineffective to remove a persistent, unacceptable odor from hydrogenated polybutene polymer of molecular weight of about 100 to about 4,000 g/mol.

EXAMPLE 4

A hydrogenated polybutene polymer of molecular weight of about 100 g/mol to about 4,000 g/mol was prepared in a manner similar to that described in Example 1. The hydrogenated polybutene polymer was distilled (1 wt.% was distilled off as overhead) in a manner similar to that described in Example 2. The main fraction was silica gel treated at a hydrogenated distilled polybutene polymer to silica gel ratio of 50:1, similar to that described in Example 2. The odor was judged very acceptable by an odor panel.

This example illustrates that a 1 wt.% distillation followed by treatment with silica gel provides a hydrogenated distilled silica gel-treated polybutene polymer having a very acceptable odor.

COMPARATIVE EXAMPLE B

A hydrogenated polybutene polymer of molecular weight of about 100 to about 4,000 g/mol, was prepared in a manner similar to that described in Example 1. The hydrogenated polybutene polymer was distilled in a manner similar to that described in Example 2. This distilled, hydrogenated polybutene polymer was judged by an odor panel to have a higher level of odor than the silica gel-treated, distilled, hydrogenated polybutene polymer of Example 4.

This example illustrates that distillation by itself is not as effective as distillation followed by treatment with silica gel.

COMPARATIVE EXAMPLE C

Polybutene polymer was hydrogenated in a manner similar to that described in Example 1 to provide a hydrogenated polybutene polymer having a molecular weight range of from about 100 g/mol to about 4,000 g/mol. The hydrogenated polybutene polymer was then nitrogen-stripped. A three-neck round-bottom 500 liter flask equipped with electric mantle, mechanical stirrer, thermowell and condensers were charged with 2,501 grams of hydrogenated polybutene polymer, molecular weight of from about 100 to about 4,000 g/mol. Temperature of the hydrogenated polybutene polymer was 360° F. Nitrogen gas (greater than 10 scfh) was bubbled through the hydrogenated polybutene polymer for a period of 15 minutes. 25.3g of distillate was collected in a 250 ml flask.

After cooling, the stripped material was submitted to an odor panel to detect any odor. The odor panel judged the hydrogenated distilled polybutene polymer (before treatment with silica gel) from Example 2 to be of a much lower odor than the hydrogenated nitrogen stripped polybutene polymer of Comparative Example C.

This example illustrates that distillation alone is more effective than nitrogen stripping alone (i.e., without treatment with silica gel).

COMPARATIVE EXAMPLE D

A hydrogenated polybutene polymer, prepared in a manner similar to Example 1, having a molecular weight range of from about 100 g/mol to about 4,000 g/mol was not distilled but was treated with silica gel as described in Example 2.

The non-distilled, but silica gel-treated hydrogenated polybutene polymer, was judged by an odor panel to be inferior in odor quality to the distilled and silica gel-treated hydrogenated polybutene polymer of Example 2.

This example illustrates that treatment with silica gel alone (without distillation) is not as effective as distillation combined with treatment with silica gel.

COMPARATIVE EXAMPLE E

Hydrogenated polybutene polymer of molecular weight of about 100 to about 4,000 g/mol, prepared in a manner as described in Example 1, was treated with attapulgite clay to remove odor. Treatment with attapulgite clay alone was ineffective in removing color to an acceptable level. Details of the clay treatment are as follows:

A) Hydrogenated polybutene polymer of molecular weight of from about 100 to about 4,000 g/mol, 800 cc, was filtered in a single pass through 40 ml of attapulgite clay, 30-60 mesh, in a 250 ml buret maintained at room temperature. The odor panel found that the filtered sample had a persistent unacceptable odor.

B) The procedure of clay treatment A) was repeated using a glass funnel equipped with a funnel heating mantle. The filtration was maintained at a temperature of 150° F. The odor panel found that the filtered product had a persistent, unacceptable odor.

C) The procedure of clay treatment B) was repeated at a temperature of 200° F. The odor panel found that the filtered product had a persistent, unacceptable odor.

D) The procedure of clay treatment B) was repeated at a temperature of 250° F. the odor panel found that the filtered product had a persistent, unacceptable odor.

The above illustrates that clay treatment alone is ineffective to remove a persistent, unacceptable odor from hydrogenated polybutene polymer of from about 100 to about 4,000 g/mol molecular weight.

EXAMPLE 5

A sample was prepared according to the manner described in Example 2, with 5 wt.% distilled off as overhead. Head space gas chromatographic analysis were preformed on the main distillate fraction before distillation, after distillation and before silica gel treatment, and on the hydrogenated distilled silica gel-treated polybutene polymer. The liquid sample was heated, a head space gas sample was drawn, and the gas chromatography was completed on the head space gas sample. Multiple analyses were run on each sample. The average and standard deviation (noted in parenthesis) of the differential voltage area count are reported in Table I, below.

TABLE I
DISAPPEARANCE OF ODOR COMPONENTS

| Retention Time | Before Distillation | After Distillation and Before silica gel Treatment | Final |
|---|---|---|---|
| 0.51 | 7,701 (598) | 0 | 55 (110) |
| 0.60 | 17,300 (402) | 72 (125) | 0 |
| 0.75 | 25,629 (815) | 469 (56) | 358 (252) |
| 0.88 | 13,866 (783) | 0 | 754 (153) |
| 1.10 | 520 (38) | 0 | 0 |
| 1.37 | 24,279 (1,679) | <50 | 1,721 (328) |
| 1.48 | 0 | 0 | 0 |
| 1.64 | 7,707 (557) | 18,959 (1,766) | 0 |
| 1.92 | 0 | 0 | 0 |
| 2.17 | 2,709 (223) | 0 | 0 |
| 2.82 | 7,246 (630) | 0 | 0 |
| 3.18 | 2,434 (188) | 0 | 0 |
| 3.69 | 3,655 (323) | 0 | 0 |
| 4.18 | 3,493 (524) | 0 | 0 |
| 6.11 | 3,504 (372) | 0 | 0 |
| 6.60 | 2,731 (270) | 0 | 0 |
| 8.14 | 1,562 (196) | 0 | 758 (879) |
| 9.03 | 2,486 (233) | 0 | 0 |
| 10.48 | 0 | 0 | 0 |
| 22.97 | 4,950 (476) | 0 | 0 |
| 24.54 | 2,157 (1,870) | 0 | 0 |

As can be seen from Table I, when the head space was analyzed by gas chromatography analysis several peaks were present before the hydrogenated polybutene was processed according to the present invention and were reduced, or disappeared, after processing.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

That which is claimed is:

1. A process for deodorizing an odorous polybutene polymer comprising:
    A) distilling a hydrogenated polybutene polymer having a number average molecular weight of from about 100 to 4,000 g/mol at a temperature of from about 290° F. to about 370° F. and at a pressure of no more than 10 mmHg (absolute);
    B) Treating the higher boiling portion of the hydrogenated distilled polybutene polymer distillation product with a silica gel at a temperature of less than about 150° F. to produce a hydrogenated, distilled, silica gel-treated polybutene polymer substantially free of odorous compounds.

2. A process for deodorizing an odorous polybutene polymer comprising:
    A) hydrogenating polybutene polymer at a temperature of from about 150° F. to about 525° F. in the presence of a catalyst, to form a substantially hydrogenated polybutene polymer containing odorous compounds;
    B) distilling a hydrogenated polybutene polymer having a number average molecular weight of from about 100 to 4,000 g/mol at a temperature of from about 290° F. to about 370° F. and at a pressure of no more than 10 mmHg (absolute) to remove a portion of the odorous compounds, and to prepare a hydrogenated, distilled polybutene polymer;
    C) treating the hydrogenated, distilled polybutene polymer with a silica gel wherein the ratio of the hydrogenated distilled polybutene polymer to the silica gel is from about 25:1 to about 200:1 at a temperature of less than about 150° F. to remove additional odorous compounds and provide a hydrogenated, distilled, silica gel-treated polybutene polymer; and
    D) recovering the hydrogenated, distilled, silica gel-treated polybutene polymer substantially free of odorous compounds.

3. The process of claim 2 wherein the hydrogenated, distilled, silica gel-treated polybutene polymer has haze —5 APHA maximum, haze-free color —10 APHA maximum and of a number average molecular weight range of from about 100 to about 4,000 g/mol.

4. The process of claim 2 wherein the hydrogenation catalyst is selected from the group consisting of nickel, platinum, and palladium.

5. The process of claim 2 wherein from about 2 wt.% to about 4 wt.% of the hydrogenated polybutene polymer is distilled off to remove a portion of the odorous compounds.

6. The process of claim 2 wherein the ratio of the hydrogenated distilled polybutene polymer to the silica gel is from about 50:to about 100:1.

7. The process of claim 2 wherein the ratio of the hydrogenated distilled polybutene polymer to the silica gel is about 50:1.

8. The process of claim 2 wherein the ratio of the hydrogenated distilled polybutene polymer to the silica gel is about 100:1.

9. The process of claim 2 wherein the silica gel is from about 28 to about 200 mesh (0.0232-0.0029 inch).

10. The process of claim 2 wherein the distillation is from about 3 mmHg to about 5 mmHg (absolute).

11. The process of claim 2 wherein from about 0.5 wt.% to about 5 wt.% of the total charge material is distilled off as overhead fraction.

* * * * *

UNITED STATES PATENT AND TRADEMARK OFFICE
CERTIFICATE OF CORRECTION

PATENT NO. : 5,177,277
DATED : January 5, 1993
INVENTOR(S) : William E. Eryman, et al It is certified that error appears in the above-indentified patent and that said Letters Patent is hereby corrected as shown below:

| Column | Line | | | |
|---|---|---|---|---|
| 11 | Table I 35 | "$\frac{\text{Retention Time}}{4.18}$" | should read | --$\frac{\text{Retention Time}}{4.81}$-- |
| 12 | 48 | "about 5:to" should read --about 5:1-- | | |

Signed and Sealed this

Fourth Day of January, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO.: 5,177,277

DATED: January 5, 1993

INVENTOR(S): William S. Eryman, James B. Lents, Yin-Chou Lin, Thomas E. Rehm, and Egils Vitands It is certified that error appears in the above-identified patent and that said Letters Patent is hereby corrected as shown below:

Patent reads:

| Col. | Line | |
|------|------|---|
| 12 | 2 | "(absolute:)" should read--(absolute) to partially remove a portion of the odorous compounds so as to form a partially treated polybutene polymer;-- |

Signed and Sealed this

Eighth Day of March, 1994

Attest:

BRUCE LEHMAN

Attesting Officer

Commissioner of Patents and Trademarks